(12) United States Patent
Wahlstrand et al.

(10) Patent No.: US 9,393,432 B2
(45) Date of Patent: Jul. 19, 2016

(54) NON-HERMETIC DIRECT CURRENT INTERCONNECT

(75) Inventors: Carl D. Wahlstrand, North Oaks, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 737 days.

(21) Appl. No.: 12/609,957

(22) Filed: Oct. 30, 2009

(65) Prior Publication Data

US 2010/0114249 A1    May 6, 2010

Related U.S. Application Data

(63) Continuation of application No. 61/110,363, filed on Oct. 31, 2008.

(51) Int. Cl.
*A61N 1/375* (2006.01)

(52) U.S. Cl.
CPC .............. *A61N 1/3754* (2013.01); *A61N 1/3752* (2013.01)

(58) Field of Classification Search
CPC ........................... A61N 1/3754; A61N 1/3752
USPC .......................... 607/36–37, 45, 63, 115–119
See application file for complete search history.

(56) References Cited

U.S. PATENT DOCUMENTS

| | | | |
|---|---|---|---|
| 3,310,051 A | 3/1967 | Schulte | |
| 3,447,160 A | 6/1969 | Teder | |
| 3,522,811 A | 8/1970 | Schwartz et al. | |
| 3,598,128 A | 8/1971 | Chardack | |
| 3,690,325 A | 9/1972 | Kenny | |
| 3,720,874 A | 3/1973 | Gorcik et al. | |
| 3,724,467 A | 4/1973 | Avery et al. | |
| 3,766,331 A | 10/1973 | Zink | |
| 3,888,260 A | 6/1975 | Fischell | |
| 3,913,587 A | 10/1975 | Newash | |
| 3,926,198 A | 12/1975 | Kolenik | |
| 3,941,135 A | 3/1976 | von Sturm et al. | |
| 4,006,748 A | 2/1977 | Schulman | |
| 4,010,760 A | 3/1977 | Kraska et al. | |
| 4,013,081 A | 3/1977 | Kolenik | |
| 4,040,412 A | 8/1977 | Sato | |
| 4,094,321 A | 6/1978 | Muto | |
| 4,256,115 A | 3/1981 | Bilitch | |

(Continued)

FOREIGN PATENT DOCUMENTS

| | | |
|---|---|---|
| DE | 3940632 | 12/1990 |
| DE | 19837912 C1 | 10/1999 |

(Continued)

OTHER PUBLICATIONS

"Surgical Process," Animation Screenshots from http://www.cochlearamerica.com/800.asp, 7 pp., last printed Feb. 3, 2004.

(Continued)

*Primary Examiner* — Rex R Holmes
(74) *Attorney, Agent, or Firm* — Shumaker & Sieffert, P.A.

(57) ABSTRACT

A modular implantable medical device (IMD) may include a non-hermetic interconnect. The non-hermetic interconnect may electrically couple a first module and a second module of the modular IMD. A conductor in the non-hermetic interconnect may conduct electrical energy from the first module to the second module under an applied direct current (DC) voltage.

2 Claims, 6 Drawing Sheets

(56) References Cited

U.S. PATENT DOCUMENTS

| | | |
|---|---|---|
| 4,266,552 A | 5/1981 | Dutcher et al. |
| 4,328,813 A | 5/1982 | Ray |
| 4,399,819 A | 8/1983 | Cowdery |
| 4,399,820 A | 8/1983 | Wirtzfeld et al. |
| 4,408,607 A | 10/1983 | Maurer |
| 4,499,907 A | 2/1985 | Kallok et al. |
| 4,503,860 A | 3/1985 | Sams et al. |
| 4,574,780 A | 3/1986 | Manders |
| 4,616,655 A | 10/1986 | Weinberg et al. |
| 4,617,913 A | 10/1986 | Eddington |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A | 11/1990 | Owens et al. |
| 5,085,644 A | 2/1992 | Watson et al. |
| 5,095,904 A | 3/1992 | Seligman et al. |
| 5,116,345 A | 5/1992 | Jewell et al. |
| 5,144,946 A | 9/1992 | Weinberg et al. |
| 5,197,332 A | 3/1993 | Shennib |
| 5,207,218 A | 5/1993 | Carpentier et al. |
| 5,218,959 A | 6/1993 | Fenster |
| 5,220,929 A | 6/1993 | Marquit |
| 5,243,977 A | 9/1993 | Trabucco et al. |
| 5,252,090 A | 10/1993 | Giurtino et al. |
| 5,271,397 A | 12/1993 | Seligman et al. |
| 5,292,342 A | 3/1994 | Nelson et al. |
| 5,312,440 A | 5/1994 | Hirschberg et al. |
| 5,314,451 A | 5/1994 | Mulier |
| 5,314,453 A | 5/1994 | Jeutter |
| 5,391,188 A | 2/1995 | Nelson et al. |
| 5,396,813 A | 3/1995 | Takeuchi et al. |
| 5,411,537 A | 5/1995 | Munshi et al. |
| 5,411,538 A | 5/1995 | Lin |
| H1465 H | 7/1995 | Stokes |
| 5,431,695 A | 7/1995 | Wiklund et al. |
| 5,433,734 A | 7/1995 | Stokes et al. |
| 5,455,999 A | 10/1995 | Owens et al. |
| 5,456,698 A | 10/1995 | Byland et al. |
| 5,458,997 A | 10/1995 | Crespi et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,573,551 A | 11/1996 | Lin et al. |
| 5,613,935 A | 3/1997 | Jarvik |
| 5,638,832 A | 6/1997 | Singer et al. |
| 5,645,586 A | 7/1997 | Meltzer |
| 5,674,260 A | 10/1997 | Weinberg |
| 5,678,559 A | 10/1997 | Drakulic |
| 5,702,430 A | 12/1997 | Slimon et al. |
| 5,741,313 A | 4/1998 | Nason et al. |
| 5,748,767 A | 5/1998 | Raab |
| 5,755,743 A | 5/1998 | Volz et al. |
| 5,769,874 A | 6/1998 | Dahlberg |
| 5,773,961 A | 6/1998 | Cameron et al. |
| 5,776,169 A | 7/1998 | Schroeppel |
| 5,792,067 A | 8/1998 | Karell |
| 5,800,535 A | 9/1998 | Howard, III |
| 5,814,095 A | 9/1998 | Müller et al. |
| 5,827,288 A | 10/1998 | Umber et al. |
| 5,836,935 A | 11/1998 | Ashton et al. |
| 5,843,150 A | 12/1998 | Adams et al. |
| 5,873,899 A | 2/1999 | Stutz, Jr. et al. |
| RE36,120 E | 3/1999 | Karell |
| 5,876,424 A | 3/1999 | O'Phelan et al. |
| 5,895,414 A | 4/1999 | Sanchez-Zambrano |
| 5,896,647 A | 4/1999 | Shkuratoff |
| 5,919,215 A | 7/1999 | Haeg et al. |
| 5,927,277 A | 7/1999 | Baudino et al. |
| 5,935,154 A | 8/1999 | Westlund |
| 5,938,689 A | 8/1999 | Fischell et al. |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,958,088 A | 9/1999 | Vu et al. |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,044,304 A | 3/2000 | Baudino |
| 6,052,623 A | 4/2000 | Fenner et al. |
| 6,061,593 A | 5/2000 | Fischell et al. |
| 6,067,474 A | 5/2000 | Schulman et al. |
| 6,091,979 A | 7/2000 | Madsen |
| 6,106,464 A | 8/2000 | Bass et al. |
| 6,112,120 A | 8/2000 | Correas |
| 6,128,538 A | 10/2000 | Fischell et al. |
| 6,131,581 A | 10/2000 | Leysieffer et al. |
| 6,134,474 A | 10/2000 | Fischell et al. |
| 6,146,390 A | 11/2000 | Heilbrun et al. |
| 6,154,677 A | 11/2000 | Leysieffer |
| 6,162,487 A | 12/2000 | Darouiche |
| 6,168,580 B1 | 1/2001 | Yardley |
| 6,176,879 B1 | 1/2001 | Reischl et al. |
| 6,205,358 B1 | 3/2001 | Haeg et al. |
| 6,214,032 B1 | 4/2001 | Loeb et al. |
| 6,218,016 B1 | 4/2001 | Tedeschi et al. |
| 6,230,049 B1 | 5/2001 | Fischell et al. |
| 6,233,488 B1 | 5/2001 | Hess |
| 6,248,080 B1 | 6/2001 | Miesel et al. |
| 6,248,126 B1 | 6/2001 | Lesser et al. |
| 6,259,951 B1 | 7/2001 | Kuzma et al. |
| 6,263,225 B1 | 7/2001 | Howard, III |
| 6,266,556 B1 | 7/2001 | Ives et al. |
| 6,269,266 B1 | 7/2001 | Leysieffer |
| 6,272,382 B1 | 8/2001 | Faltys et al. |
| 6,283,997 B1 | 9/2001 | Garg et al. |
| 6,308,101 B1 | 10/2001 | Faltys et al. |
| 6,324,428 B1 | 11/2001 | Weinberg et al. |
| 6,324,433 B1 | 11/2001 | Errico |
| 6,327,502 B1 | 12/2001 | Johansson et al. |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,366,813 B1 | 4/2002 | DiLorenzo |
| 6,384,628 B1 | 5/2002 | Lacey et al. |
| 6,405,079 B1 | 6/2002 | Ansarinia |
| 6,415,184 B1 | 7/2002 | Ishikawa et al. |
| 6,427,086 B1 | 7/2002 | Fischell et al. |
| 6,436,422 B1 | 8/2002 | Trogolo et al. |
| 6,445,956 B1 | 9/2002 | Laird et al. |
| 6,456,256 B1 | 9/2002 | Amundson et al. |
| 6,456,886 B1 | 9/2002 | Howard, III et al. |
| 6,480,743 B1 | 11/2002 | Kirkpatrick et al. |
| 6,490,486 B1 | 12/2002 | Bradley |
| 6,498,951 B1 | 12/2002 | Larson et al. |
| 6,505,077 B1 | 1/2003 | Kast et al. |
| 6,516,227 B1 | 2/2003 | Meadows et al. |
| 6,516,808 B2 | 2/2003 | Schulman |
| 6,517,476 B1 | 2/2003 | Bedoya et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,647,296 B2 | 11/2003 | Fischell et al. |
| 6,648,914 B2 | 11/2003 | Berrang et al. |
| 6,671,544 B2 | 12/2003 | Baudino |
| 6,721,602 B2 | 4/2004 | Engmark et al. |
| 6,726,678 B1 | 4/2004 | Nelson et al. |
| 6,736,770 B2 | 5/2004 | Leysieffer et al. |
| 6,782,292 B2 | 8/2004 | Whitehurst |
| 6,788,974 B2 | 9/2004 | Bardy et al. |
| 6,805,998 B2 | 10/2004 | Jenson et al. |

(56) References Cited

U.S. PATENT DOCUMENTS

| | | |
|---|---|---|
| 6,850,802 B2 | 2/2005 | Holsheimer |
| 6,882,881 B1 | 4/2005 | Lesser et al. |
| 6,899,976 B2 | 5/2005 | Larson et al. |
| 6,963,780 B2 | 11/2005 | Ruben et al. |
| 6,966,044 B2 | 11/2005 | Reuland et al. |
| 6,977,124 B2 | 12/2005 | Probst et al. |
| 6,994,933 B1 | 2/2006 | Bates |
| 7,003,352 B1 | 2/2006 | Whitehurst |
| 7,010,351 B2 | 3/2006 | Firlik et al. |
| 7,033,326 B1 | 4/2006 | Pianca et al. |
| 7,103,415 B2 | 9/2006 | Probst et al. |
| 7,107,097 B2 | 9/2006 | Stern et al. |
| 7,107,099 B1 | 9/2006 | O'Phelan et al. |
| 7,110,819 B1 | 9/2006 | O'3 Hara |
| 7,167,760 B2 | 1/2007 | Dawant et al. |
| 7,212,864 B2 | 5/2007 | Wahlstrand et al. |
| 7,242,982 B2 | 7/2007 | Singhal et al. |
| 7,259,586 B2 | 8/2007 | Peterson et al. |
| 7,263,401 B2 | 8/2007 | Scott et al. |
| 7,317,947 B2 | 1/2008 | Wahlstrand et al. |
| 7,392,089 B2 | 6/2008 | Wahlstrand et al. |
| 7,454,251 B2 | 11/2008 | Rezai et al. |
| 7,529,586 B2 | 5/2009 | Wahlstrand et al. |
| 7,596,399 B2 | 9/2009 | Singhal et al. |
| 7,596,408 B2 | 9/2009 | Wahlstrand et al. |
| 7,702,380 B1 | 4/2010 | Dean |
| 8,095,200 B2 | 1/2012 | Quaid, III |
| 2001/0033953 A1 | 10/2001 | Takeuchi et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0037756 A1 | 3/2002 | Jacobs et al. |
| 2002/0042630 A1 | 4/2002 | Bardy et al. |
| 2002/0042634 A1 | 4/2002 | Bardy et al. |
| 2002/0051550 A1 | 5/2002 | Leysieffer |
| 2002/0059049 A1 | 5/2002 | Bradbury et al. |
| 2002/0068958 A1 | 6/2002 | Bardy et al. |
| 2002/0072770 A1 | 6/2002 | Pless et al. |
| 2002/0077670 A1 | 6/2002 | Archer et al. |
| 2002/0087201 A1 | 7/2002 | Firlik et al. |
| 2002/0099412 A1 | 7/2002 | Fischell et al. |
| 2002/0103510 A1 | 8/2002 | Bardy et al. |
| 2002/0107546 A1 | 8/2002 | Ostroff et al. |
| 2002/0147498 A1 | 10/2002 | Tallarida et al. |
| 2002/0161403 A1 | 10/2002 | Meadows et al. |
| 2002/0165588 A1 | 11/2002 | Fraley et al. |
| 2002/0169485 A1 | 11/2002 | Pless et al. |
| 2002/0177882 A1 | 11/2002 | DiLorenzo |
| 2003/0004428 A1 | 1/2003 | Pless et al. |
| 2003/0004546 A1 | 1/2003 | Casey |
| 2003/0017372 A1 | 1/2003 | Probst et al. |
| 2003/0023256 A1 | 1/2003 | Estes et al. |
| 2003/0040781 A1 | 2/2003 | Sunderland et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0091893 A1 | 5/2003 | Kishiyama et al. |
| 2003/0109903 A1 | 6/2003 | Berrang et al. |
| 2003/0120320 A1 | 6/2003 | Solom |
| 2003/0125786 A1 | 7/2003 | Gliner et al. |
| 2003/0130706 A1 | 7/2003 | Sheffield et al. |
| 2003/0143895 A1 | 7/2003 | Sommer et al. |
| 2003/0163134 A1 | 8/2003 | Riedel et al. |
| 2003/0171787 A1 | 9/2003 | Money et al. |
| 2003/0204229 A1 | 10/2003 | Stokes |
| 2003/0228042 A1 | 12/2003 | Sinha |
| 2004/0015070 A1 | 1/2004 | Liang et al. |
| 2004/0030245 A1 | 2/2004 | Noble et al. |
| 2004/0073252 A1 | 4/2004 | Goldberg et al. |
| 2004/0082977 A1 | 4/2004 | Engmark et al. |
| 2004/0102828 A1 | 5/2004 | Lowry et al. |
| 2004/0172090 A1 * | 9/2004 | Janzig et al. .................. 607/45 |
| 2004/0173221 A1 | 9/2004 | Singhal et al. |
| 2004/0176673 A1 | 9/2004 | Wahlstrand et al. |
| 2004/0176750 A1 | 9/2004 | Nelson et al. |
| 2004/0176814 A1 | 9/2004 | Singhal et al. |
| 2004/0176815 A1 | 9/2004 | Janzig et al. |
| 2004/0176816 A1 | 9/2004 | Singhal et al. |
| 2004/0176817 A1 | 9/2004 | Wahlstrand et al. |
| 2004/0176818 A1 | 9/2004 | Wahlstrand et al. |
| 2004/0176819 A1 | 9/2004 | Wahlstrand et al. |
| 2004/0181263 A1 | 9/2004 | Balzer et al. |
| 2004/0186528 A1 | 9/2004 | Ries et al. |
| 2004/0243481 A1 | 12/2004 | Bradbury et al. |
| 2004/0257882 A1 | 12/2004 | Stackhouse et al. |
| 2005/0003268 A1 | 1/2005 | Scott et al. |
| 2005/0004618 A1 | 1/2005 | Scott et al. |
| 2005/0004619 A1 | 1/2005 | Wahlstrand et al. |
| 2005/0004620 A1 | 1/2005 | Singhal et al. |
| 2005/0004637 A1 | 1/2005 | Singhal et al. |
| 2005/0004640 A1 | 1/2005 | Kolberg |
| 2005/0015128 A1 | 1/2005 | Rezai et al. |
| 2005/0033378 A1 | 2/2005 | Sheffield et al. |
| 2005/0070781 A1 | 3/2005 | Dawant et al. |
| 2005/0070971 A1 | 3/2005 | Fowler et al. |
| 2005/0075679 A1 | 4/2005 | Gliner et al. |
| 2005/0159792 A1 | 7/2005 | Ridder |
| 2005/0228249 A1 | 10/2005 | Boling |
| 2005/0245806 A1 | 11/2005 | Singhal et al. |
| 2005/0245984 A1 | 11/2005 | Singhal et al. |
| 2006/0004422 A1 | 1/2006 | De Ridder |
| 2006/0094951 A1 | 5/2006 | Dean et al. |
| 2006/0116743 A1 | 6/2006 | Gibson et al. |
| 2006/0129205 A1 | 6/2006 | Boveja et al. |
| 2006/0149336 A1 | 7/2006 | Meadows |
| 2006/0173510 A1 | 8/2006 | Besio et al. |
| 2006/0184210 A1 | 8/2006 | Singhal et al. |
| 2006/0184220 A1 | 8/2006 | Singhal et al. |
| 2006/0195156 A1 | 8/2006 | Singhal et al. |
| 2006/0239052 A1 | 10/2006 | McGrath et al. |
| 2006/0253825 A1 | 11/2006 | McGrath et al. |
| 2006/0259841 A1 | 11/2006 | Savage et al. |
| 2007/0074732 A1 | 4/2007 | Singhal et al. |
| 2007/0118243 A1 | 5/2007 | Schroeder et al. |
| 2007/0185539 A1 | 8/2007 | Singhal et al. |
| 2007/0255338 A1 | 11/2007 | Wahlstrand et al. |
| 2008/0021511 A1 | 1/2008 | Scott et al. |
| 2008/0065173 A1 | 3/2008 | Wahlstrand et al. |
| 2009/0281623 A1 | 11/2009 | Kast et al. |
| 2009/0292327 A1 | 11/2009 | Singhal et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |

FOREIGN PATENT DOCUMENTS

| | | |
|---|---|---|
| EP | 1145735 A2 | 10/2001 |
| EP | 1145736 A2 | 10/2001 |
| FR | 1 516 654 | 3/1968 |
| GB | 1 161 579 | 8/1969 |
| WO | 92/20402 | 11/1992 |
| WO | 99/06108 | 2/1999 |
| WO | 99/34758 | 7/1999 |
| WO | 99/55408 | 11/1999 |
| WO | 00/13743 | 3/2000 |
| WO | 00/40295 | 7/2000 |
| WO | 01/10369 | 2/2001 |
| WO | 01/028622 | 4/2001 |
| WO | 01/39830 | 6/2001 |
| WO | 01/41858 | 6/2001 |
| WO | 01/60450 | 8/2001 |
| WO | 01/97906 | 12/2001 |
| WO | 02/05590 | 1/2002 |
| WO | 02/056637 | 7/2002 |
| WO | 02/083207 | 7/2002 |
| WO | 02/083208 | 10/2002 |
| WO | 02/083233 | 10/2002 |
| WO | 03/026739 | 4/2003 |
| WO | 03/076012 | 9/2003 |
| WO | 2004/043536 | 5/2004 |
| WO | 2004/052458 | 6/2004 |
| WO | 2004/052459 | 6/2004 |
| WO | 2004/060484 | 7/2004 |

(56) References Cited

FOREIGN PATENT DOCUMENTS

OTHER PUBLICATIONS

"Candidates Brochure," http://www.cochlearamerica.com/pdfs/candidatebrochglobal.pdf, 14 pp., Aug. 19, 2002.
"Research and Development," http://www.cochlearamericas.com/384.asp, 1 pg., last printed Feb. 3, 2004.
"The World Leader in cochlear implants—revolutionizing hearing for adults and infants," http://www.cochlear.com, 1 pg., last printed Feb. 3, 2004.
"Cochlear: innovator of the Nucleus 3 cochlear implant system," http://www.cochlearamericas.com, 1 pg., last printed Feb. 3, 2004.
"What is a Cochlear Implant," http://www.cochlearamericas.com/What/161.asp, 1 pg., last printed Feb. 3, 2004.
"ESPrit 3G Speech Processor," http://www.cochlearamericas.com/591.asp, 2 pp., last printed Feb. 3, 2004.
"Nucleus 3 System," http://www.cochlearamericas.com/Products/465.asp, 1 pg., last printed Feb. 3, 2004.
"Internal Components: Nucleus 24 Cochlear Implants," http://www.cochlearamericas.com/374.asp, 1 pg., last printed Feb. 3, 2004.
"Nucleus 24 Contour," http://www.cochlearamericas.com/568.asp, 2 pp., last printed Feb. 3, 2004.
"Nucleus 24 M," http://www.cochlearamericas.com/372.asp, 1 pg., last printed Feb. 3, 2004.
"Nucleus 24 K," http://www.cochlearamericas.com/371.asp, 1 pg., last printed Feb. 3, 2004.
"Nucleus 24 Double Array," http://www.cochlearamericas.com/370.asp, 1 pg., last printed Feb. 3, 2004.
"Nucleus 24 ABI: Auditory Brainstem Implant," http://www.cochlearamericas.com/373.asp, 2 pp., last printed Feb. 3, 2004.
"Nucleus Speech Processors," http://www.cochlearamericas.com/629.asp, 1 pg., last printed Feb. 3, 2004.
"Sprint: body worn speech processor," http://www.cochlearamericas.com/1010.asp, 1 pg., last printed Feb. 3, 2004.
"Cochlear," http://www.cochlearamericas.com/Recipients/978.asp, 3 pp., last printed Feb. 3, 2004.
Answers.com, www.answers.com, defined: discrete components, acessed on Mar. 2, 2007, 2 pp.
Porex Surgical Products group, "new MEDPOR Cranial Dome Implant," www.porexsurgical.com (1 pg) Aug. 20, 2002.

\* cited by examiner

NON-HERMETIC DIRECT CURRENT INTERCONNECT

This application claims the benefit of U.S. Provisional Application No. 61/110,363, entitled, "NON-HERMETIC DIRECT CURRENT INTERCONNECT," and was filed on Oct. 31, 2008, the entire content of which is incorporated herein by reference.

TECHNICAL FIELD

The disclosure relates to electrical connectors for implantable medical devices.

BACKGROUND

Depending on the application for which they are implanted in a patient, implantable medical devices (IMDs) may include a variety of electrical and/or mechanical components. In many cases, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from titanium because of its desirable rigidity and biocompatibility.

The size and shape of an IMD housing is dependent on the sizes and shapes of the components of the IMD. Large components common to most IMDs include a battery and a circuit board that carries digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing.

Recently, modular IMDs that place components of the IMD in separate modules have been proposed. For example, a modular IMD may include a battery housed in a first module, digital and/or analog circuitry housed in a second module, and a telemetry coil. A common encapsulation member formed of silicone, polyurethane, or another biocompatible polymer may at least partially encapsulate the modules of the modular IMD. One or more hermetic interconnects, which may include a metallic covering over one or more conductors, may electrically interconnect the modules.

SUMMARY

In general, the present disclosure is directed to a modular implantable medical device (IMD) that includes a non-hermetic interconnect. The non-hermetic interconnect may electrically couple a first module and a second module in the modular IMD. A conductor in the non-hermetic interconnect may conduct energy, e.g., for power or communication, from the first module to the second module under an applied direct current (DC) voltage.

The non-hermetic interconnect may include a single conductor or a plurality of conductors. The conductors may be straight or coiled, and in some examples, a first conductor may be separated from a second conductor by a distance along at least a portion of a length of the conductors. For example, the first conductor may be separated from the second conductor by at least 1 millimeter (mm) for at least a portion of a length of the conductors. As another example, the first conductor may be separated from the second conductor by at least 1 centimeter (cm) for at least a portion of a length of the conductors.

The non-hermetic interconnect may be coupled to at least one of the first module and the second module via a hermetic feedthrough. The hermetic feedthrough provides an access in a hermetic housing of the at least one of the first and second modules through which the conductor may pass. The hermetic feedthrough may comprise glass, such as Cabal-12 or lanthium borate glass.

The modular IMD may include a single non-hermetic interconnect or a plurality of non-hermetic interconnects. In some examples, a first non-hermetic interconnect may be separated from a second non-hermetic interconnect by a distance along at least a portion of a length of the non-hermetic interconnects. The distance may be, for example, at least 1 mm, or at least 1 cm.

The non-hermetic interconnect may be flexible, and may permit relative intermodule motion between the modules of the modular IMD. In some examples, however, the non-hermetic interconnect may include a mechanical feature that reduces or limits the relative intermodule motion in at least one direction.

In one example, the disclosure provides a modular IMD comprising a first module comprising a first feedthrough and a second feedthrough, wherein the first feedthrough and the second feedthrough are separated by at least about 1 millimeter, a second module, an electronic component within one of the first module and the second module, and a non-hermetic interconnect electrically coupling the first module and the second module. The non-hermetic interconnect comprises a first conductor and a second conductor, wherein the first conductor passes through the first feedthrough and the second conductor passes through the second feedthrough. The electronic component applies a DC voltage to at least one of the first conductor and the second conductor to transfer at least one of energy or a communication signal from one of the first module and the second module to the other of the first module and second module via the at least one of the first conductor and the second conductor.

In another example, the disclosure provides a modular IMD comprising a first module, a second module, an electronic component within one of the first module and the second module, and a non-hermetic interconnect electrically coupling the first module and the second module. The non-hermetic interconnect comprises a first conductor and a second conductor. The first conductor and the second conductor are separated by at least 1 millimeter for substantially an entire length of the non-hermetic interconnect. The electronic component applies a DC voltage to at least one of the first conductor and the second conductor to transfer at least one of energy or a communication signal from one of the first module and the second module to the other of the first module and the second module via the at least one of the first conductor and the second conductor.

In another example, the disclosure provides a modular IMD comprising a first module comprising a first metallic housing, a second module comprising second metallic housing, an electronic component within one of the first module and the second module, and a non-hermetic interconnect electrically coupling the first module and the second module. The non-hermetic interconnect comprises a metallic conductor, and the electronic component applies a DC voltage to the metallic conductor to transfer at least one of energy or a communication signal from the first module to the second module via the metallic conductor.

Examples according to this disclosure may provide advantages. For example, a metallic covering of a hermetic interconnect may lead to a reduced lifetime of an IMD in which it is included because of failure of the hermetic interconnect due to material flex fatigue from relative intermodule motion. A non-hermetic interconnect according to this disclosure need not include the metallic covering of a hermetic interconnect, and therefore may be more flexible and more resistant to material flex fatigue failure than a hermetic interconnect.

The details of one or more examples are set forth in the accompanying drawings and the description below. Other features, objects, and advantages will be apparent from the description and drawings, and from the claims.

DETAILED DESCRIPTION

Figure 1:
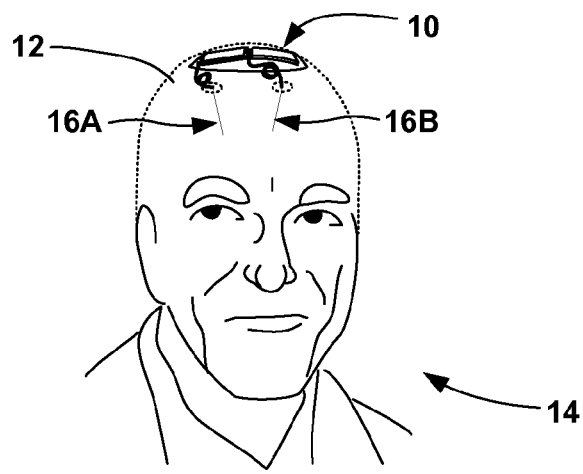
FIG. 1 is a conceptual diagram illustrating an example modular implantable medical device (IMD) implanted on a cranium of a patient.

FIG. 1 is a conceptual diagram illustrating an example modular implantable medical device (IMD) 10 that includes at least two modules and a non-hermetic interconnect electrically coupling a first module and a second module. Because components of modular IMD 10 are separated into at least two modules, modular IMD 10 may have a reduced profile, which allows modular IMD 10 to be more cosmetically appealing, comfortable, and clinically acceptable when implanted, for example, on the cranium 12 of a patient 14. In other examples, a modular IMD according to this disclosure may be implanted in any other location within the body of patient 14, such as the chest, abdomen, back, pelvis, or buttocks.

The non-hermetic interconnect may provide advantages for modular IMD 10. For example, compared to a hermetic interconnect, the non-hermetic interconnect may have increased flexibility and improved flex fatigue life. In addition, the non-hermetic interconnect may increase longevity of modular IMD 10 due to improved flex fatigue life.

The non-hermetic interconnect may include a single conductor or a plurality of conductors. The conductors may be straight or coiled, and in some examples, a first conductor may be separated from a second conductor by a distance along at least a portion of a length of the conductors. For example, the first conductor may be separated from the second conductor by at least 1 mm for at least a portion of a length of the conductors. As another example, the first conductor may be separated from the second conductor by at least 1 cm for at least a portion of a length of the conductors.

The non-hermetic interconnect may be coupled to at least one of the first module and the second module via a hermetic feedthrough. The hermetic feedthrough provides an entrance through a hermetic housing of the at least one of the first and second modules for the conductor to pass through. The hermetic feedthrough may comprise glass, such as Cabal-12 or lanthium borate glass.

Modular IMD 10 may include a single non-hermetic interconnect or a plurality of non-hermetic interconnects. In some examples, a first non-hermetic interconnect may be separated from a second non-hermetic interconnect by a distance along at least a portion of a length of the non-hermetic interconnects. The distance may be, for example, at least 1 mm, or at least 1 cm.

The non-hermetic interconnect may be flexible, and may permit relative intermodule motion between the modules of the modular IMD 10. In some examples, however, the non-hermetic interconnect may include a mechanical feature that reduces or limits the relative intermodule motion in at least one direction.

The non-hermetic interconnect of may enable conduction of current between modules of modular IMD 10 via a DC voltage. This may simplify the construction of modular IMD 10, and may reduce the size of modular IMD 10, as will be described in further detail below.

The non-hermetic interconnect can be applied within a modular IMD 10 of any structure. For purposes of illustration, however, the invention will be described herein as a modular IMD 10 housed in a member that at least partially encapsulates one or more housings of the modules and, and generally serves to provide a smooth interface between the modules and the body tissue. In other examples, through, the modular IMD 10 may not include a member that at least partially encapsulates one or more housing of the modules.

As will be described in below, modular IMD 10 comprises a plurality of separately housed and flexibly interconnected modules. By distributing components of modular IMD 10 among modules rather than including them within a single, rigid housing, modular IMD 10 may be shaped and configured for implantation at locations within patient 14 for which implantation of a conventional IMD is deemed undesirable or inapplicable. Further, the flexibility of the interconnection between modules of modular IMD 10 may allow multiples degrees of freedom of movement between the modules, which in turn may allow the implantable medical device to conform to such areas, and in particular examples, to conform to surfaces within patient 14 such as the surface of cranium 12.

In the illustrated example, modular IMD 10 is coupled to two leads 16A and 16B (collectively "leads 16") that extend through holes within cranium 12 and into the brain of patient 14. In exemplary examples, each of leads 16 carries a plurality of electrodes, and modular IMD 10 delivers stimulation to the brain of patient 14 via the electrodes. Modular IMD 10 may be coupled to any number of leads 16, and in some examples is not coupled to any leads 16. In some examples, for example, modular IMD 10 may carry integrated electrodes.

Because modular IMD 10 can be implanted on cranium 12 of patient 14 rather more remotely from the brain of patient 14, such as within a subclavicular region of patient 14, the problems associated with the use of long leads needed to allow a remotely implanted IMD to access the brain may be diminished or avoided. These problems include the requirement of tunneling under the scalp and the skin of the neck, increased surgery and recovery time, an additional procedure under general anesthesia, risk of infection or skin erosion along the track through which the leads are tunneled, and risk of lead fracture due to torsional and other forces caused by normal head and neck movements.

Figure 2:
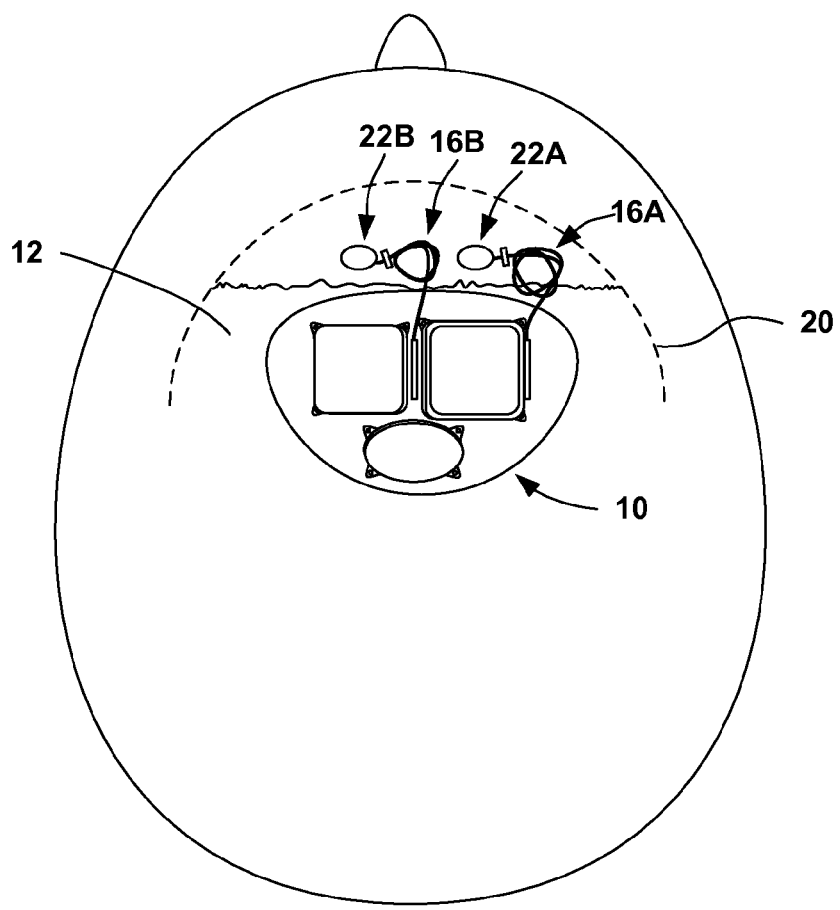
FIG. 2 is a top-view diagram further illustrating the module IMD from FIG. 1 implanted on the cranium of the patient.

FIG. 2 is a top-view diagram further illustrating modular IMD 10 implanted on cranium 12 of patient 14. In order to implant modular IMD 10 on cranium 12, an incision 20 is made through the scalp of patient 14, and a resulting flap of skin is pulled back to expose the desired area of cranium 12. The incision may, as shown in FIG. 2, be generally shaped like a "C." Such an incision is commonly referred to as a "C-flap" incision.

Holes 22A and 22B (collectively "holes 22") are drilled through cranium 12, and leads 16 are inserted through holes 22 and into the brain of patient 14. Caps such as burr hole caps may be placed over holes 22 as is known in the art. Leads 16 are connected to modular IMD 10, either directly or via a lead extension, and modular IMD 10 is placed at least partially within a pocket formed using a hand or a tool beneath the scalp behind holes 22.

Once positioned as desired on cranium 12 within the pocket, modular IMD 10 may then be fixed to cranium 12 using an attachment mechanism such as bone screws. The skin flap may be closed over modular IMD 10, and the incision may be stapled or sutured. The location on cranium 12 at which modular IMD 10 is illustrated as implanted in FIG. 2 is merely an example, and modular IMD 10 can be implanted anywhere on the surface of cranium 12.

Because of the flexibility that may be provided by non-hermetic interconnects of modular IMD 10 and/or a member of IMD 10 that at least partially encapsulates the modules of IMD 10 and provides a smooth interface between the modules and body tissue, modular IMD 10 may be manipulated during implantation such that it substantially conforms to cranium 12. In some examples, a surgeon can manipulate modular IMD 10 into conformance with cranium 12 while IMD 10 is on cranium 12 and fix modular IMD 10 into place using bone screws or the like. In other examples, the clinician may manipulate modular IMD 10 into conformance with cranium 12 with IMD 10 on and/or off of cranium 12, and IMD 10 may substantially retain the form into which it is manipulated.

As mentioned above, modular IMD 10 may deliver stimulation to the brain of patient 14 to, for example, provide deep brain stimulation (DBS) therapy, or to stimulate the cortex of the brain. Cortical stimulation may involve stimulation of the motor cortex. Modular IMD 10 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular IMD 10 is not limited to delivery of stimulation to the brain of patient, and may be employed with leads 16 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular IMD 10 is not limited to implantation on cranium 12. Indeed, modular IMD 10 may be implanted anywhere within patient 14. For example, modular IMD 10 can be implanted within the neck of patient 14, and deliver stimulation to the vagus nerve or the cervical region of the spinal cord.

Modular IMD 10 may alternatively be implanted within a pectoral region or the abdomen of patient 14 to act as a diaphragmatic pacer, or to provide any of the monitoring and therapy delivery functions known in the art to be associated with cardiac pacemakers. Further, modular IMD 10 may be implanted in the upper buttock region and deliver spinal cord, urological or gastrological stimulation therapy, or may be configured to be implanted within the periphery, e.g., limbs, of patient 14 for delivery of stimulation to the muscles and/or peripheral nervous system of patient 14. Additional implant locations may include the abdomen, e.g., for gastric stimulation. As is the case with cranium 12, the modularity of IMD 10 may enable implantation at some of these example locations for which implantation of conventional IMDs is generally deemed undesirable.

Modular IMD 10 is not limited to examples that deliver stimulation. In some examples, modular IMD 10 may additionally or alternatively monitor one or more physiological parameters and/or the activity of patient 14, and may include sensors for these purposes. Where a therapy is delivered, modular IMD 10 may operate in an open loop mode (also referred to as non-responsive operation), or in a closed loop mode (also referred to as responsive). Modular IMD 10 may also provide warnings based on the monitoring.

As discussed above, the ability of a modular IMD 10 according to the present disclosure to be implanted close to a region within patient 14 to be monitored enables the use of shorter leads 16. Shorter leads 16 may advantageously improve the accuracy of such sensors by reducing noise attributable to leads 16. Shorter leads 16 may also advantageously reduce the negative effects of imaging techniques such as magnetic resonance imaging "MRI" on a person implanted with IMD 10. Within an MRI machine, leads act as antennas positioned very close to an antenna tower, therefore using shorter leads 16 reduces an amount of energy induced onto IMD 10 from the MRI machine.

Further, in some examples modular IMD 10 can additionally or alternatively deliver a therapeutic agent to patient 14, such as a pharmaceutical, biological, or genetic agent. Modular IMD 10 may be coupled to a catheter, and may include a pump or other mechanism to deliver the therapeutic agent via the catheter.

Figure 3:
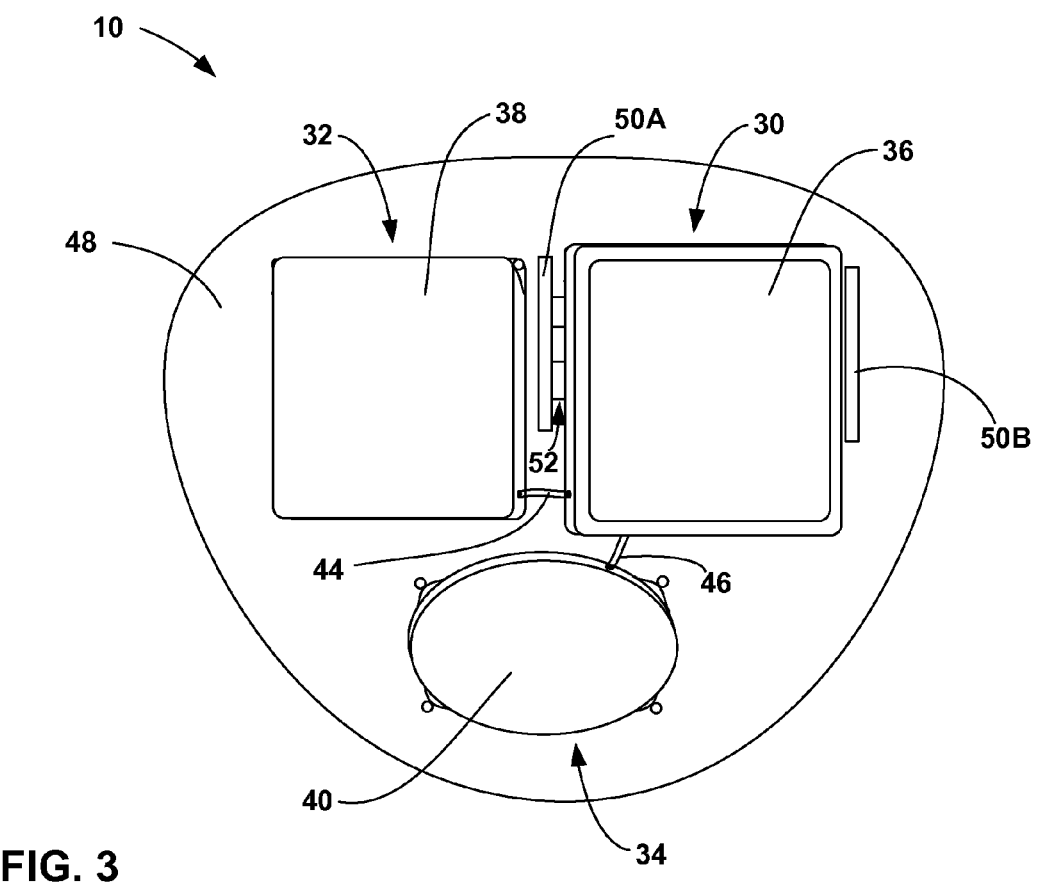
FIG. 3 is a top-view diagram further illustrating the modular IMD of FIG. 1.

FIG. 3 is a top-view diagram further illustrating modular IMD 10. In the illustrated example, modular IMD 10 includes three modules: an electronics or control module 30, a power module 32, and a recharge module 34. As shown in FIG. 3, modules 30, 32 and 34 include separate housings 36, 38 and 40, respectively.

Control module 30 includes components within the housing. In some examples, the components comprise control electronics, e.g., electronics that control the monitoring and/or therapy delivery functions of modular IMD 10, such as a microprocessor. Control module 30 may also include circuits for telemetry communication with external programmers or other devices within the housing. Housing 36 of control module 30 may be hermetic in order to protect the components therein, and in some examples is formed of a rigid material, such as titanium, stainless steel, or a ceramic. In some examples, housing 36 may be a low-profile, concave housing to substantially conform to a patient's cranium.

Power module 32 includes a battery housed within housing 38. The battery provides power for components of other modules, such as the components within control module 30. The battery may be any battery suitable for use within an IMD.

Housing 38 may be hermetic, and may be formed of titanium, stainless steel, or a ceramic. Power module 32 may include an insulator within housing 38 to electrically isolate housing 38 from the battery.

Including the battery in power module 32 separate from control module 32 may reduce a thickness and overall size of housing 36 and housing 38, which may then reduce a profile of IMD 10. The low profile of IMD 10 permits IMD 10 to be deployed effectively, comfortably and cosmetically within patient 14. In one example of the invention, IMD 10 including has a maximum thickness of between approximately 1 mm and approximately 5 mm. The use of a reduced profile may reduce the risk of infection, skin erosion and cosmetic issues related to the implantation of IMD 10.

Where the battery comprises a rechargeable battery, modular IMD 10 may include recharge module 34. Recharge module 34 includes a recharge coil (not shown) within housing 40. The recharge coil inductively receives energy from an external recharging unit (not illustrated) through the skin of patient 14 to recharge the battery. The recharge coil may be formed of windings of copper or another highly conductive material. Housing 40 need not be hermetic, and may be formed of materials such as silicone, polymers and ceramics.

Housings 36, 38 and 40 may have any shape, including the round, coin shape and rectangular shapes with rounded edges illustrated in FIG. 3. Further, one or more surfaces of one or more of housings 36, 38 and 40 may be concave along at least one axis, and preferably along two perpendicular axes.

Modules 30, 32 and 34 can be configured in a variety of ways, and the configuration illustrated in FIG. 3 is merely an example. Further, modular IMD 10 can include any number of modules, and may include other types of modules instead of or in addition to a control module 30, a power module 32, and a recharge module 34. For example, modular IMD 10 can include a module within another module, such as power module 32 within control module 30. Further, modular IMD 10 can include additional power modules, modules that include additional memory that is accessible by the components of control module 30, modules that include reservoirs for storing therapeutic agents and pumps for delivering therapeutic agents to patient 14, or modules that include sensors sensing physiological parameters, such as pressures, blood flows, an activity level, or an orientation of patient 14.

Power module 32 is coupled to control module 30 by a non-hermetic interconnect 44, which encloses an electrical conductor that allows transmission of energy from the battery of power module 32 to components such as the components within control module 30. Non-hermetic interconnect 44 may couple to at least one of control module 30 and power module 32 through a feedthrough, particularly in examples in which housing 36 or housing 38 is metallic, such as titanium. The feedthrough may be hermetic, and may be formed of, for example, glass. The construction of non-hermetic interconnect 44 and/or the feedthrough(s) may allow non-hermetic interconnect 44 to transfer electrical energy from the battery in power module 32 to electronics in control module 30 via a DC voltage. Non-hermetic interconnect 44 may include at least one conductor, which may comprise a biocompatible conductive material, such as, for example, MP-35N, Pt, or a silver-cored conductor. Non-hermetic interconnect 44 may also include a biocompatible material that encapsulates and insulates the conductor, such as, for example, silicon, polyurethane, or another polymer.

In the illustrated example, the components of control module 30 regulate the recharging and discharging of the battery within power source module 32. Consequently, as shown in FIG. 3, recharge module 34 is coupled to control module 30 by a flexible interconnect 46 that encloses an electrical conductor that allows transmission of energy inductively received by the recharge coil within recharge module 34 to control module 30. Energy is transferred on the electrical conductor via a charge-balanced voltage, and flexible interconnect 46 may be made of any material including titanium, stainless steel, nitinol, ceramics, silicone, polyurethane or other polymers.

Non-hermetic interconnect 44 may be flexible in a one or more direction to provide modules 30 and 32 with at least one degree of freedom of motion with respect to each other. In some examples, non-hermetic interconnect 44 provides at least three degrees of motion, and the degrees of motion provided may include rotational motion. In some examples, non-hermetic interconnect 44 may include mechanical features that limit flexibility in one or more direction, as will be described in further detail below.

As shown in FIG. 3, modular IMD 10 may include a member 48, which may be flexible and made of a soft biocompatible material. Member 48 at least partially encapsulates one or more of housings 36, 38 and 40, and generally serves to provide a smooth interface between the modules encapsulated by member 48 and the body tissue. Member 48 may integrate modules 30, 32 and 34 into a desired form factor, but, where flexible, allow relative intermodule motion. In some examples, member 48 incorporates mechanical features to restrict intermodule motion to certain directions or within certain ranges. Member 48 may be made from silicone, and in some examples may be made from two or more materials of differing flexibility, such as silicone and a polyurethane. An exemplary polyurethane for this purpose is Tecothane®, which is commercially available from Hermedics Polymer Products, Wilmington, Mass. Member 48 may also be referred to as an "overmold," but use of the term "overmold" herein is not intended to limit the invention to examples in which member 48 is a molded structure. Member 48 may be a molded structure, or may be a structure formed by any process.

Member 48 can be shaped to contour to cranium 12, e.g., may be concave along at least one axis, and may be contoured at its edges to prevent skin erosion on the scalp of patient 14. The flexibility and shape of member 48 may, in some examples, improve the comfort and cosmetic appearance of modular IMD 10 under the scalp, and may make IMD 10 more clinically acceptable by, for example, reducing the likelihood of skin erosion.

In the illustrated example, modular IMD 10 also includes lead connector modules 50A and 50B (collectively "lead connector modules 50") formed within member 48 to receive leads 16 or lead extensions coupled to leads 16. Conductors 52 extend from lead connector modules 50 to hermetic feedthroughs (not illustrated) within housing 36 of control module 30. Lead connector modules 50 may be formed anywhere within member 48. In examples where member 48 includes a rigid material in addition to a flexible material, the rigid material may form at least part of lead connector modules 50 to secure leads 16 or lead extensions, and to protect conductors 52 from damage that may result from flexing within member 48.

Figure 4:
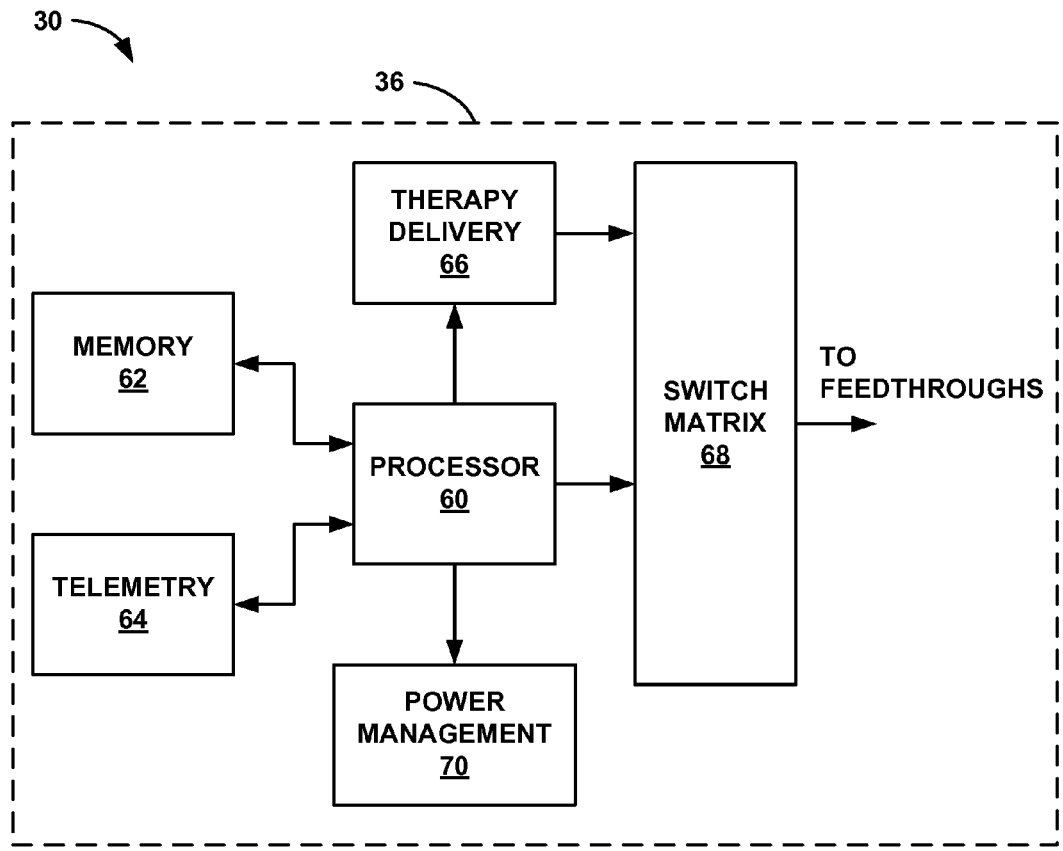
FIG. 4 is a block diagram illustrating a control module of the modular IMD from FIG. 3.

FIG. 4 is a block diagram illustrating control module 30 of modular IMD 10. As described above, control module 30 includes components, such as control electronics that control the functioning of modular IMD 10 within housing 36. The components include a processor 60, which may take the form of a microprocessor, digital signal processor (DSP), application specific integrated circuit (ASIC), field-programmable gate array (FPGA), or other logic circuitry.

Control module 30 also includes a memory 62, such as a read-only memory (ROM), random access memory (RAM), electronically-erasable programmable ROM (EEPROM), flash memory, or the like. Memory 62 may store program instructions that may be executed by processor 60 and thereby control the functioning of modular IMD 10. Processor 60 may also store data collected during treatment and/or monitoring of patient 14 within memory 62.

In some examples, control module 30 includes telemetry circuitry 64, which enables processor 60 to communicate with other devices such as an external programming device via radio-frequency communication. Telemetry circuitry 64 may include a telemetry coil (not illustrated), which may be fabricated of windings of copper or another highly conductive material. The configuration and location of the telemetry coil within housing 36 may be dictated by the available space within housing 36 and the communication requirements of telemetry circuitry 64.

In some examples, modular IMD 10 delivers electrical stimulation, and more particularly, control module 30 includes therapy delivery circuitry 66 within housing 36 that generates electrical stimulation. In some examples, therapy delivery circuitry 66 comprises circuits for the generation of electrical stimulation in the form of pulses, such as capacitors and switches. In examples in which modular IMD 10 is a neurostimulator coupled to leads 16 that include a plurality of electrodes, therapy delivery circuitry 66 may deliver the pulses to a switch matrix 68, which comprises an array of switches. In such examples, processor 60 interacts with switch matrix 68 to select electrodes for delivery of generated stimulation pulses. Based on the selections made by processor 60, switch matrix 68 delivers the pulses to conductors that pass through feedthroughs in housing 36 and to electrical contacts on leads 16 that are electrically coupled to the desired electrodes carried by leads 16. In other examples, control module 30 need not include switch matrix 68, and may instead include a plurality of circuits for the generation of electrical stimulation, each of which may be coupled to one or more electrodes.

The illustrated components of control module 30 receive energy from the battery within power source module 32 via non-hermetic interconnect 44 (FIG. 3). In some examples in which the battery is rechargeable, control module 30 receives energy inductively captured by recharge module 34 via non-hermetic interconnect member 46, and includes power management circuitry 70 that controls the recharging and discharging of the battery. Power management circuitry 70 may ensure that the battery is not overcharged, over-discharged, or harmed. In some examples, power management circuitry 70 includes circuits to measure voltages, currents or temperatures associated with the battery, or rates of change of these parameters, and controls recharging and discharging according to the measured values. Power management circuitry 70 may also include circuits, such as rectifier circuits, for converting charge-balanced voltages, e.g., AC voltages, provided by a recharge coil (not shown) into net DC voltages for recharging the battery.

Figure 5:
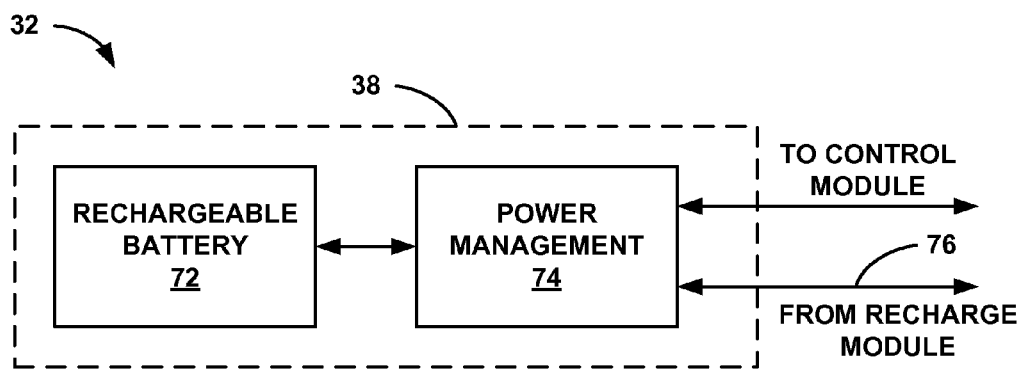
FIG. 5 is a block diagram illustrating a power module of the modular IMD from FIG. 3.

FIG. 5 is a block diagram illustrating power module 32 of modular IMD 10. Power module 32 includes a rechargeable battery 72 within housing 38. In the illustrated example, in which power module 32 directly receives energy inductively captured by recharge module 34 via a non-hermetic interconnect member 76, power source module 32 also includes power management circuit 74 that controls the recharging and discharging of battery 72. As described above with reference to power management circuitry 70 of control module 30 illustrated in FIG. 4, power management circuitry 74 may ensure that battery 72 is not overcharged, over-discharged, or harmed. In some examples, power management circuitry 74 includes circuits to measure voltages, currents or temperatures associated with battery 72, or rates of change of these parameters, and controls recharging and discharging of battery 72 according to the measured values.

Power management circuitry 74 may also include circuits, such as rectifier circuits, for converting charge-balanced voltages, e.g., AC voltages, provided by a recharge coil (not shown) into DC voltages for recharging battery 72. In some examples, power management circuitry 74 may also include modulating circuits, i.e., circuits that enable power management circuit 74 to deliver energy to control module 30 in the form of charge-balanced voltages on an electrical conductor. In such examples, control module 30 includes circuits, such as rectifier circuits, to convert the charge-balanced voltages to DC voltages for use by components of control module 30.

However, power management circuitry 74 may not include modulating circuits in some examples. As described in further detail below, non-hermetic interconnect 44 may allow power management circuit 74 to deliver energy to control module 30 via a DC voltage, thus negating the need for power management circuit 74 to modulate the DC voltage of battery 72 to charge-balanced voltages for transfer of energy to control module 30.

Figure 6:
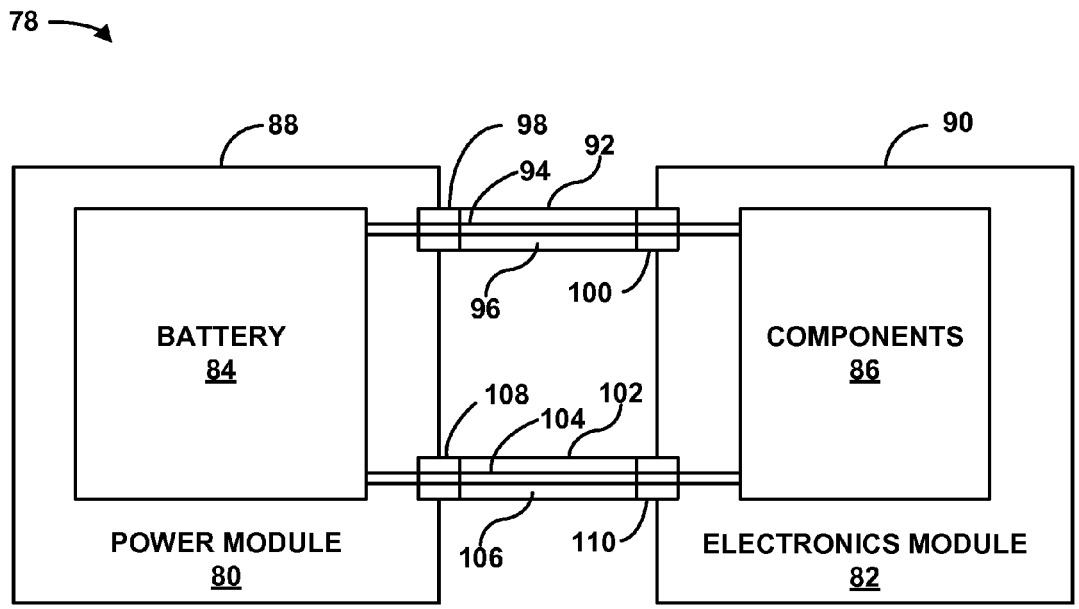
FIG. 6 is a block diagram illustrating an example modular IMD including two non-hermetic interconnects electrically coupling a power module and an electronics module.

FIG. 6 is a block diagram illustrating an example modular IMD 78 including a power module 80 and an electronics module 82 electrically coupled by a first non-hermetic interconnect 92 and a second non-hermetic interconnect 102. Power module 80 includes a battery 84 housed within housing 88. Battery 84 provides power for components of other modules, such as components 86 within a housing 90 of electronics module 82. Battery 84 may be any battery suitable for use within an IMD, such as, for example, a lithium ion battery. Housing 88 may be hermetic, and may be formed of titanium, stainless steel, or a ceramic. Power module 80 also may include an insulator within housing 88 to electrically isolate housing 88 from battery 84.

Electronics module 82 includes components 86 housed within housing 90. In some examples, components 86 comprise control electronics, e.g., electronics that control the monitoring and/or therapy delivery functions of modular IMD 78, such as a microprocessor. Electronics module 82 may also include within the housing circuits for telemetry communication with external programmers or other devices. Housing 90 of control module 82 may be hermetic in order to protect the components therein, and in some examples may be formed of a rigid material, such as titanium, stainless steel, or a ceramic. In some examples, housing 90 may be a low-profile, concave housing to substantially conform to a patient's cranium.

First and second non-hermetic interconnects 92 and 102 include first conductor 94 and second conductor 104, respectively. First conductor 94 electrically couples battery 84 to components 86, and is encapsulated in a first non-hermetic material 96 along at least the portion of the length of first conductor 94 between first hermetic feedthrough 98 and second hermetic feedthrough 100. Similarly, second conductor 104 electrically couples battery 84 to components 86, and is encapsulated in a second non-hermetic material 106 for at least the portion of second conductor 104 between third hermetic feedthrough 108 and fourth hermetic feedthrough 110.

Battery 84 may transfer power to components 86 by applying a DC voltage to one or both of conductors 94 and 96. This is in contrast to electrical energy transmission over conductors in conventional non-hermetic interconnects, which require transfer of electrical energy via a charge-balanced voltage (AC voltage) to reduce or eliminate the likelihood of current shunting or corrosion of the conductors. However, non-hermetic interconnects 92 and 102 facilitate electrical energy transfer over conductors 94 and 96 via an applied DC voltage.

Transferring electrical energy from battery 84 via an applied DC voltage may simplify construction of power module 80 and/or electronics module 82. For example, transferring electrical energy from battery 84 via an applied DC voltage may negate the requirement for DC-to-AC voltage conversion circuitry in power module 80. This may simplify construction of power module 80, and may also reduce a size of power module 80, and thus, modular IMD 78. In some examples, transferring electrical energy from battery 84 via an applied DC voltage may negate the requirement for AC-to-DC voltage conversion circuitry in electronics module 82. This may simplify construction of electronics module 82, and may also reduce a size of electronics module 82.

Non-hermetic materials 96 and 106 may comprise, for example, a polymer, such as silicone, polyurethane, ethylene tetrafluoroethylene (ETFE), or the like. The polymer may permit non-hermetic interconnects 92 and 102 to be flexible, and may decrease the effects of mechanical stress placed on non-hermetic interconnects 92 and 102 compared to a hermetic interconnect. For example, mechanical stress may be placed on one or both of non-hermetic interconnects 92 and 102 be relative motion between power module 80 and electronics module 82. Decreasing the mechanical stress placed on non-hermetic interconnects 92 and 102 may increase the flex fatigue life, which may increase the useful lifetime of module IMD 78.

While non-hermetic interconnects 92 and 102 may be flexible, interconnects 92 and 102 may also include materials or structures that limit flexibility of the interconnects 92 and 102, as will be described in further detail below. Limiting flexibility of at least one of non-hermetic interconnects 92 and 102 may limit relative inter-module motion of power module 80 and electronics module 82. This may be desirable in some examples to, for example, inhibit migration of modular IMD 78 within a patient.

First conductor 94 passes through first hermetic feedthrough 98 in housing 88 of power module 80 and second hermetic feedthrough 100 in housing 90 of electronics module 82. Similarly, second conductor 104 passes through third hermetic feedthrough 108 in housing 88 of power module 80 and fourth hermetic feedthrough 110 in housing 90 of electronics module 82. First and third hermetic feedthroughs 98 and 108 may contribute to the hermetic sealing of power module 80 to prevent exchange of fluids or gases between the interior of housing 88 (e.g., battery 84) and the exterior environment (e.g., a body of a patient). This may prevent corrosion or shorting of battery 84, and may protect the patient from adverse effects of non-biocompatible fluids or gases produced by or leaking from battery 84. In the same way, second and fourth hermetic feedthroughs 100 and 110 may contribute to the hermetic sealing of electronics module 82.

Hermetic feedthroughs 98, 100, 108 and 110 may comprise, for example, a hermetic glass and a conductor housed in the hermetic glass. In some examples, at least one of hermetic feedthroughs 98, 100, 108 and 110 may comprise Cabal-12, available from Sandia National Laboratories. Cabal-12 includes approximately 20 percent by mole (mol. %) CaO, approximately 20 mol. % Mg), approximately 20 mol. % $Al_2O_3$, and approximately 20 mol. % $B_2O_3$. Further details regarding use of Cabal-12 as a hermetic glass in a feedthrough may be found in U.S. patent application Ser. No. 11/116,968, entitled, "GLASS-TO-METAL FEEDTHROUGH SEALS HAVING IMPROVED DURABILITY PARTICULARLY UNDER AC OR DC BIAS," and filed Apr. 28, 2005, the entire content of which is incorporated herein by reference. Cabal-12 may facilitate sealing of hermetic feedthroughs 98, 100, 108, and/or 110 to housing 88 or housing 90, respectively, at temperatures lower than an alpha/beta transition temperature of titanium. This may reduce or substantially prevent grain growth or warping of housing 88 or housing 90, when the housing 88 or 90 is formed from titanium or a titanium alloy.

In other examples, at least one of hermetic feedthroughs 98, 100, 108 and 110 may comprise lanthium borate glass. Lanthium borate glass may include a range of compositions. For example a lanthium borate glass may include between 0 mol. % and approximately 20 mol. % CaO, between 0 mol. % and approximately 20 mol. % MgO, between 0 mol. % and approximately 20 mol. % SrO, between 0 mol. % and approximately 5 mol. % $La_2O_3$, between 5 mol. % and approximately 10 mol. % $SiO_2$, and between 10 mol. % and approximately 20 mol. % $Al_2O_3$. In one example, a lanthium borate glass comprises approximately 20 mol. % CaO, approximately 20 mol. % MgO, approximately 15 mol. % $Al_2O_3$, approximately 5 mol. % $La_2O_3$, approximately 30 mol. % $B_2O_3$, and approximately 10 mol. % $SiO_2$. In some examples, a lanthium borate glass may further include $MnO_2$. Further details regarding exemplary lanthium borate glasses may be found in U.S. patent application Ser. No. 12/469,823, entitled, "INSULATOR FOR FEEDTHROUGH," and filed on May 21, 2009, the entire content of which is incorporated herein by reference.

Similar to Cabal-12, a lanthium borate glass may facilitate sealing of hermetic feedthroughs 98, 100, 108, and/or 110 to housing 88 or housing 90, respectively, at temperatures lower than an alpha/beta transition temperature of titanium. This may reduce or substantially prevent grain growth or warping of housing 88 or housing 90, when the housing 88 or 90 is formed from titanium or a titanium alloy. Additionally, a lanthium borate glass may have a sufficiently low viscosity such that the lanthium borate glass flows under its own weight (i.e., does not require externally applied pressure) and forms a hermetic seal with housing 88 or housing 90 at a temperature below 870° C.

Another example of a hermetic glass from which hermetic feedthroughs 98, 100, 108, or 110 may be formed is CVP (CaBA1-Variation-Promeon), as described in U.S. Pat. No. 6,090,503, entitled, "BODY IMPLANTED DEVICE WITH ELECTRICAL FEEDTHROUGH," and filed Apr. 16, 1998, the entire content of which is incorporated herein by reference.

The conductor of at least one of hermetic feedthroughs 98, 100, 108, or 110 may comprise a biocompatible conductive material, such as, for example, tantalum (Ta), niobium, (Nb), titanium (Ti), platinum (Pt), iridium (Ir), or an alloy including at least one of Ta, Nb, Ti, Pt, or Ir.

Hermetic feedthroughs 98, 100, 108 and 110 may also contribute to reducing or preventing corrosion of first conductor 94 or second conductor 104. Corrosion of first or second conductors 94 or 104 may be induced or accelerated when current is shunted between a housing 88 or 90 and one of conductors 94 or 104. Current shunting between housing 88 and first conductor 94, for example, may induce galvanic corrosion between housing 88 and first conductor 94. Galvanic corrosion occurs when a metal corrodes preferentially when in electrical contact with another metal and immersed in an electrolyte. These conditions may exist when an imperfection is present in non-hermetic material 96 that allows a bodily fluid (an electrolyte) to come in contact with first conductor 94 and housing 88, which may be metallic. However, hermetic feedthroughs 98 increase the path length required for current to shunt between first or second conductors 94 or 104 and housing 88 or 90, thus reducing the likelihood of shunting and the occurrence of corrosion.

First non-hermetic interconnect 92 and second non-hermetic interconnect 102 may also be separated by some distance, as illustrated in FIG. 6, to reduce the likelihood of current shunting between first conductor 94 and second conductor 104. For example, first non-hermetic interconnect 92 and second non-hermetic interconnect 102 may be separated by at least about 1 mm for substantially the entire length of interconnects 92 and 102. In some examples, it may be desirable to separate first non-hermetic interconnect 92 and second non-hermetic interconnect 102 by as great a distance as possible, which may be limited only by the size of power module 80 and electronics module. For example, in some examples first non-hermetic interconnect 92 and second non-hermetic interconnect 102 may be separated by greater than about 1 cm for at least a portion of the lengths of interconnects 92 and 102. In other examples, first non-hermetic interconnect 92 and second non-hermetic interconnect 102 may be separated by greater than about 1 cm for substantially the entire lengths of interconnects 92 and 102.

Separating first non-hermetic interconnect 92 and second non-hermetic interconnect 102 may be accomplished by, for example, separating first hermetic feedthrough 98 and third hermetic feedthrough 108 by a certain distance, and/or separating second hermetic feedthrough 100 and fourth hermetic feedthrough 104 by a certain distance. For example, first hermetic feedthrough 98 and third hermetic 108 may be separated by greater than about 1 mm, or greater than about 1 cm. Similarly, second hermetic feedthrough 100 and fourth hermetic feedthrough 110 may be separated by greater than about 1 mm, or greater than about 1 cm.

Alternatively or additionally, first non-hermetic interconnect 92 and second non-hermetic interconnect 102 may be mechanically coupled by one or more structures that maintain a desired separation, and which may limit the intermodule motion between power module 80 and electronics module 82.

FIG. 6 illustrates two non-hermetic interconnects 92 and 100 electrically coupling power module 80 and electronics module 82. In other examples, modular IMD 78 may include more than two non-hermetic interconnects. For example, modular IMD 78 may include three or more non-hermetic interconnects. An increased number of non-hermetic interconnects may increase the probability of imperfections in or damage to a non-hermetic interconnect used in modular IMD 78, however, so it may be desired to limit the number of non-hermetic interconnects.

Additionally, while FIG. 6 does not illustrate an overmold or encapsulating member that encapsulates at least a portion of one or both of power module 80 and electronics module 82, modular IMD 78 may include a member that encapsulates one or both of power module 80 and electronics module. The member may provide a substantially smooth interface between the modules at least partially encapsulated by the member and body tissue, and may be flexible to allow relative intermodule motion. The member may also incorporate mechanical features to restrict intermodule motion in one or more directions. The member may comprise, for example, silicone, and may be formed from two or more materials of differing flexibility, such as silicone and polyurethane. In some examples, the member may also at least partially encapsulate one or both non-hermetic interconnects 92 and 102.

Figure 7:
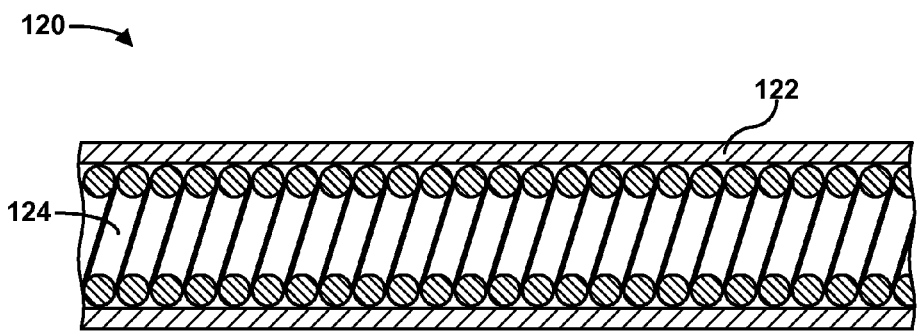
FIG. 7 is a cross-sectional diagram illustrating an example non-hermetic interconnect.

FIG. 7 illustrates an example of a non-hermetic interconnect 120 that includes a non-hermetic sheath 122 which encapsulates a coiled conductor 124. Non-hermetic sheath 122 may comprise a polymer, as described above. For example, non-hermetic sheath 122 may comprise polyurethane, silicone, ETFE, or the like. Non-hermetic sheath 122 may loosely encapsulate coiled conductor 124, which may allow freedom of motion between non-hermetic sheath 122 and coiled conductor 124 and increase flexibility of non-hermetic interconnect 120. Alternatively, non-hermetic sheath 122 may tightly encapsulate coiled conductor 124, and may form a friction fit between the outer surfaces of coiled conductor 124 and the inner surface of non-hermetic sheath 122. This may reduce the relative motion between coiled conductor 124 and non-hermetic sheath 122, and may reduce the flexibility of non-hermetic interconnect 120. In other examples, non-hermetic sheath 122 may be molded over coiled conductor 124 and may by physically or chemically bound to coiled conductor 124. For example, coiled conductor 124 may be embedded within non-hermetic sheath 122. This may further reduce relative motion between coiled conductor 124 and non-hermetic sheath 122, and further reduce flexibility of non-hermetic interconnect 120.

In addition to providing protection from the surrounding environment (e.g., bodily fluids) for coiled conductor 124, non-hermetic sheath may electrically insulate coiled conductor 124 from the surrounding environment, and helps to prevent shunting of current between, for example, coiled conductor 124 and a metallic housing, such as, housings 88 and 90.

Coiled conductor 124 may comprise an insulated braided stranded wire, an insulated solid wire, a non-insulated braided stranded wire, or a non-insulated solid wire. Insulating coiled conductor 124 may provide further environmental protection and electrical insulation to coiled conductor 124 in addition to non-hermetic sheath 122. This may further reduce the likelihood of current shunting between coiled conductor 124 and a metallic housing, such as, housings 88 and 90. For example, in the event of damage to non-hermetic sheath 122, insulation encapsulating coiled conductor 124 may still provide electrical insulation between coiled conductor 124 and bodily fluids, and thus, the metallic housing or another conductive material with which coiled conductor 124 may establish a circuit.

Coiled conductor 114 may include a biocompatible metal or alloy, such as, for example, MP-35N, platinum, or another highly conductive, biocompatible metal or alloy. In some examples, coiled conductor 114 may comprise an alloy including platinum, which is highly corrosion-resistant.

Figure 8:
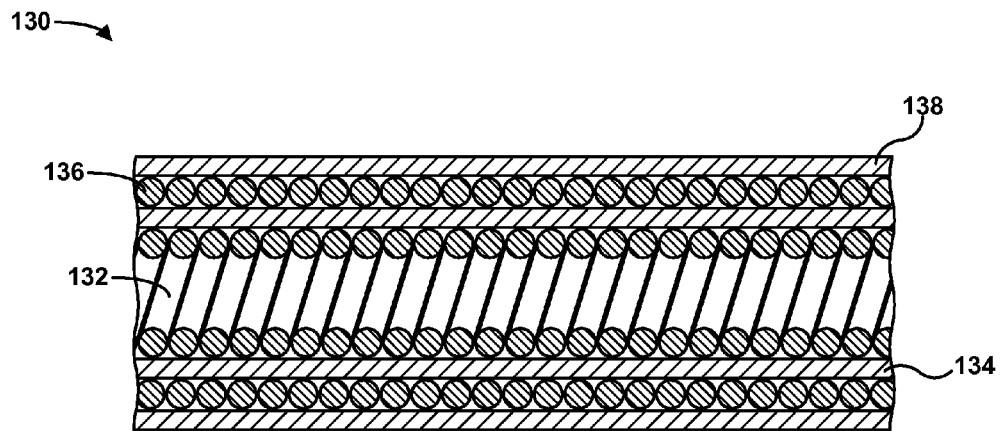
FIG. 8 is a cross-sectional diagram illustrating another example non-hermetic interconnect.

While FIG. 7 illustrates a non-hermetic interconnect 120 including a single coiled conductor 124, in other examples, a non-hermetic interconnect 120 may include a conductor which is not coiled, or may include more than one coiled conductor. For example, as FIG. 8 illustrates, a non-hermetic interconnect 130 may include a first conductor 132 and a second conductor 136. First conductor 132 may be coiled in relatively a relatively small coil, while second conductor 136 may be coiled in a relatively larger coil surrounding and substantially coaxial with the first coil. One or both of first and second conductors 132 and 136 may be insulated, and non-hermetic interconnect 130 may further include an insulative sheath 134 between first conductor 132 and second conductor 136, and an outer insulative sheath 138 radially outward from second conductor 136. In some examples, first and second conductors 132 and 136 may be separated by some distance along substantially the entire length of the non-hermetic interconnect 130, such as at least 1 mm, or at least 1 cm.

Returning now to FIG. 7, in some examples, non-hermetic interconnect 120 may further include a material or structure that modifies a flexibility of non-hermetic interconnect 120. For example, non-hermetic interconnect 120 may include materials with different elastic moduli to modify the flexibility of non-hermetic interconnect 120. For instance, non-hermetic interconnect 120 may comprise a strip or band of material with a relatively high elastic modulus, such as a rigid polymer or metal, which may limit the flexibility of non-hermetic interconnect 120 in one or more directions along a length of non-hermetic interconnect 120. The strip or band of material may be present for at least a portion of the length or circumference of non-hermetic interconnect, and may be present for substantially the entire length or circumference of non-hermetic interconnect 120.

As another example, non-hermetic sheath 122 may comprise different thicknesses along the length or circumference of sheath 122, which may increase the flexibility (e.g., a thinner wall thickness) or decrease the flexibility (e.g., a thicker wall thickness) of non-hermetic interconnect.

Figure 9:
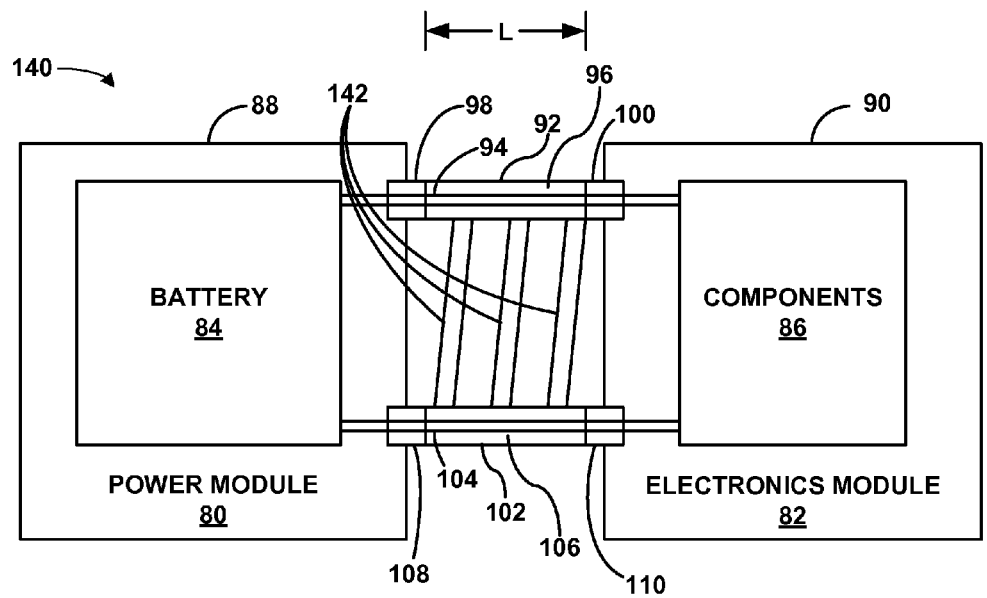
FIG. 9 is a block diagram illustrating an example modular IMD including two non-hermetic interconnects electrically coupling a power module and an electronics module.

FIG. 9 illustrates another example modular IMD 140, which includes power module 80, electronics module 82, first non-hermetic interconnect 92, and second non-hermetic interconnect 102. First non-hermetic interconnect 92 and second non-hermetic interconnect 102 are mechanically coupled by a plurality of reinforcements 142, which may limit relative motion between first non-hermetic interconnect 92 and second non-hermetic interconnect 102. Reinforcements 142 may comprise a wide range of materials including a metal, ceramic, or polymer, and in some examples, may comprise a polymer or other substantially non-conductive material to reduce the probability that a current may travel between first conductor 94 and second conductor 104 along one or more of reinforcements 142 in the event of damage to non-hermetic material 96 or 106.

Reinforcements 142 may limit the relative motion between first non-hermetic interconnect 92 and second non-hermetic interconnect 102 in one or more directions. For example, reinforcements 142 may prevent first non-hermetic interconnect 92 and second non-hermetic interconnect 102 from separating beyond a certain distance (e.g., the length of reinforcements 142, or a distance somewhat greater than the length of reinforcements 142, when reinforcements 142 are flexible). As another example, reinforcements 142 may lessen the likelihood or prevent first non-hermetic interconnect 92 and second non-hermetic interconnect 102 from coming within a certain distance of each other. In some examples, reinforcements 142 may limit rotational motion between first non-hermetic interconnect 92 and second non-hermetic interconnect 102, alternatively or in addition to controlling, e.g., limiting, the distance between interconnects 92.

In this way, reinforcements 142 may also reduce or limit relative motion between power module 80 and electronics module 82. By limiting the relative motion between first non-hermetic interconnect 92 and second non-hermetic interconnect 102, the distance and/or rotational position between power module 80 and electronics module 82 may be substantially fixed, or may be limited to certain configurations. In some examples, this may reduce migration of modular IMD 130.

Although FIG. 9 illustrates three reinforcements 142, other examples may include more or fewer reinforcements 142. For example, some examples may include a single reinforcement, which may vary in length up to the length, L, of non-hermetic interconnects 92 and 102, or may comprise a length less than length L. The single reinforcement may comprise longitudinal or latitudinal slots or openings formed in the reinforcement to modify or increase flexibility of the reinforcement. In other examples, modular IMD 130 may include two reinforcements 142, or at least four reinforcements 142.

Figure 10:
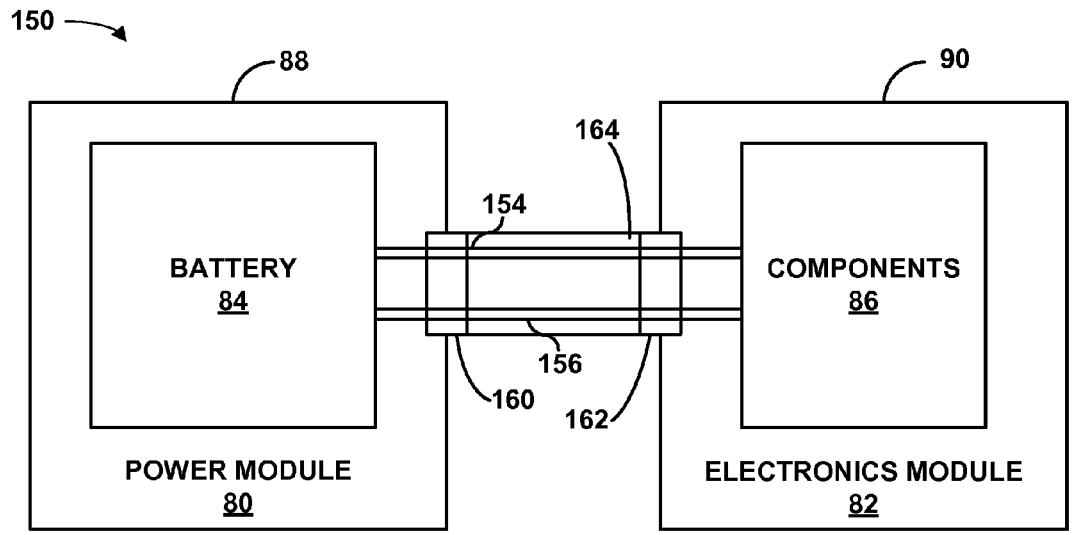
FIG. 10 is a block diagram illustrating an example modular IMD including a non-hermetic interconnect electrically coupling a power module and an electronics module.

FIG. 10 is a block diagram illustrating an example of a modular IMD 150 including a power module 80 and an electronics module 82, which are mechanically and electrically coupled by a single non-hermetic interconnect 152. More specifically, battery 84 in power module 80 is electrically coupled to components 86 in electronics module 82 by a first conductor 154 and second conductor 156, both of which are encapsulated in non-hermetic interconnect 152.

Battery 84 may transfer power to components 86 by applying a DC voltage to one or both of conductors 154 and 156. This is in contrast to electrical energy transmission over conductors in conventional non-hermetic interconnects, which require transfer of electrical energy via a charge-balanced voltage (AC voltage) to reduce or eliminate the likelihood of current shunting or corrosion of the conductors. However, non-hermetic interconnect 152 facilitates electrical energy transfer over conductors 154 and 156 via an applied DC voltage.

Transferring electrical energy from battery 84 via an applied DC voltage may simplify construction of power module 80 and/or electronics module 82. For example, transferring electrical energy from battery 84 via an applied DC voltage may negate the requirement for DC-to-AC voltage conversion circuitry in power module 80. This may simplify construction of power module 80, and may also reduce a size of power module 80, and thus, modular IMD 78. In some examples, transferring electrical energy from battery 84 via an applied DC voltage may negate the requirement for AC-to-DC voltage conversion circuitry in electronics module 82. This may simplify construction of electronics module 82, and may also reduce a size of electronics module 82.

In some examples, utilizing a single non-hermetic interconnect 152 to electrically and mechanically couple power module 80 and electronics module 82 may provide advantages compared to utilizing two or more non-hermetic interconnects (e.g., first and second non-hermetic interconnects 92 and 102). For example, utilizing a single non-hermetic interconnect 152 may enable the use of a single hermetic feedthrough 160 in housing 88 of power module 80 and a single hermetic feedthrough 162 in housing 90 of electronics module 82. This may lower the probability of a leak or other failure at an interface of hermetic feedthrough 160 and housing 88 or hermetic feedthrough 162 and housing 90.

In the example illustrated in FIG. 10, first conductor 154 and second conductor 156 may be separated by a distance to reduce or minimize risk of current shunting between first conductor 154 and second conductor 156. For example, first conductor 154 and second conductor 156 may be separated by at least about 1 mm for substantially the entire length of non-hermetic interconnect 152. In some examples, it may be desirable to separate first conductor 154 and second conductor 156 by a greater distance such as, for example, greater than about 1 cm for at least a portion of the lengths of non-hermetic interconnect 152. In other examples, first conductor 154 and second conductor 156 may be separated by greater than about 1 cm for substantially the entire length of non-hermetic interconnect 142.

As described above with reference to FIGS. 7 and 8, conductors 154 and 156 may comprise coiled conductors or non-coiled conductors. In examples in which at least one of first conductor 154 and second conductor 156 is a coiled conductor, conductors 154 and 156 may extend generally parallel, as illustrated in FIG. 10, or may be aligned coaxially with each other, as described with reference to FIG. 8. For example, first conductor 154 may be coiled in a coil with a relatively narrow diameter, and second conductor 156 may be coiled radially outward from and coaxial with first conductor 154.

One or both of first conductor 154 and second conductor 156 may be encapsulated loosely within non-hermetic material 164, which may allow relative motion between first conductor 154, second conductor 156 and non-hermetic material 164, and may increase flexibility of non-hermetic interconnect 152. Alternatively, one or both of first conductor 154 and second conductor 156 may be encapsulated within non-hermetic material 164 such that a relatively tight friction fit exists between first conductor 154 and non-hermetic material 164 and/or second conductor 156 and non-hermetic material 164. This may reduce the relative motion permitted between first conductor 154, second conductor 156, and non-hermetic material 164, which may reduce the flexibility of non-hermetic interconnect 152. In other examples, one or both of first conductor 154 and second conductor 156 may be mechanically or chemically bound to non-hermetic material 164, such as, for example, embedded within non-hermetic material 164. This may further reduce relative motion permitted between first conductor 154, second conductor 156, and non-hermetic material 164, which may reduce the flexibility of non-hermetic interconnect 152.

Figure 11:
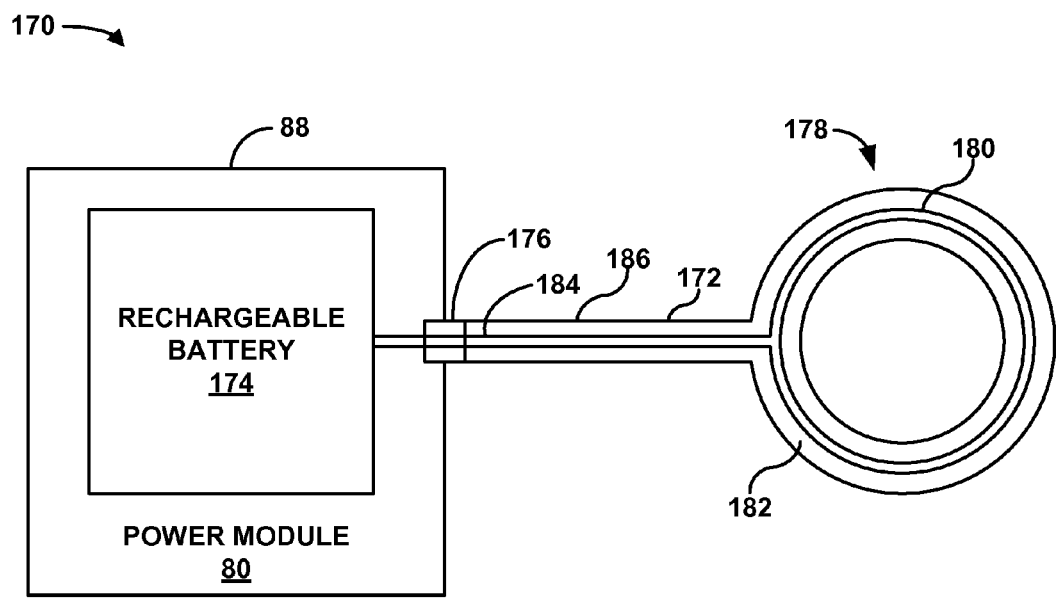
FIG. 11 is a block diagram illustrating an example modular IMD including a non-hermetic interconnect electrically coupling a power module and a recharge module.

FIG. 11 is a block diagram that illustrates a modular IMD 170 including a power module 80 electrically and mechanically coupled to a recharge module 178 by a non-hermetic interconnect 172. Power module 80 includes a housing 88, which encloses a rechargeable battery 174. Housing 88 may be hermetic, and may be formed by, for example, titanium.

Recharge module 178 includes a recharge coil 180 encapsulated in an encapsulation material 182. Recharge coil 180 may be formed of windings of copper or another highly conductive material. Recharge coil 180 inductively receives energy from an external recharging unit (not illustrated) through the skin of a patient to recharge rechargeable battery 174. Encapsulation material 182 need not be hermetic, and may be formed of materials such as silicone, polymers and ceramics. In some examples, recharge module 178 may be enclosed in a housing, which may be formed of, for example, titanium.

Recharge coil 180 receives energy from an external recharging unit by inductively coupling to the external recharging unit and transmits the energy via a charge-balanced (AC) voltage to rechargeable power module 80. As described in further detail above, power module 80 may include circuitry to convert the AC voltage to DC voltage for charging rechargeable battery 174.

Non-hermetic interconnect 172 may include one or more conductors 184 for transferring energy received by recharge coil 180 to power module 80. Non-hermetic interconnect 172 couples with hermetic feedthrough 176, which may comprise, for example, glass, and provides passage for conductor 174 through housing 88. Non-hermetic interconnect 172 may comprise, for example, silicone, polyurethane, ETFE, or the like, and may be flexible. In addition, as described above, non-hermetic interconnect 172 may include mechanical features that limit flexibility of interconnect 172.

Various examples have been described. However, a person of ordinary skill in the art will recognize that various modifications may be made to the described examples. For example, although described primarily with reference to examples in which the non-hermetic interconnect is used to transfer energy for powering or charging a component in another module, in other examples, a non-hermetic interconnect is additionally or alternatively conducts a DC voltage for communication with another module, e.g., via a communication signal imposed on a DC bias voltage. These and other examples are within the scope of the following claims.

The invention claimed is:

1. A modular implantable medical device (IMD) comprising: a first module; a second module; an electronic component within one of the first module and the second module; and a non-hermetic interconnect electrically coupling the first module and the second module, wherein the non-hermetic interconnect comprises a first conductor and a second conductor, wherein the first conductor and the second conductor are separated by at least 1 millimeter for substantially an entire length of the non-hermetic interconnect, and wherein the electronic component applies a DC voltage to at least one of the first conductor and the second conductor to transfer at least one of energy or a communication signal from one of the first module and the second module to the other of the first module and the second module via the at least one of the first conductor and the second conductor wherein at least one of the first conductor and the second conductor connect to at least one of the first module and the second module through a hermetic feedthrough that is comprised of lanthium borate glass.

2. A modular implantable medical device (IMD) comprising: a first module comprising a first metallic housing and a hermetic feedthrough; a second module comprising second metallic housing; an electronic component within one of the first module and the second module; and a non-hermetic interconnect electrically coupling the first module and the second module, wherein the non-hermetic interconnect comprises a metallic conductor, and wherein the electronic component applies a DC voltage to the metallic conductor to transfer at least one of energy or a communication signal from the first module to the second module via the metallic conductor and wherein the hermetic feedthrough comprises lanthium borate glass.

* * * * *